United States Patent [19]
Ouchi

[11] Patent Number: 6,013,095
[45] Date of Patent: Jan. 11, 2000

[54] ENDOSCOPIC GRASPING TOOL

[75] Inventor: Teruo Ouchi, Tokyo, Japan

[73] Assignee: Asahi Kogaku Kogyo Kabushiki Kaisha, Tokyo, Japan

[21] Appl. No.: 09/063,390

[22] Filed: Apr. 21, 1998

[30] Foreign Application Priority Data

Apr. 24, 1997 [JP] Japan ..................... 9-107063

[51] Int. Cl.[7] .............. A61B 17/28; A61B 17/42
[52] U.S. Cl. ............................. 606/205; 606/207
[58] Field of Search .................. 606/207, 205, 606/208

[56] References Cited

U.S. PATENT DOCUMENTS 5,476,479  12/1995  Green et al. ..................... 606/205
5,562,678  10/1996  Booker et al. ..................... 606/113

Primary Examiner—Michael Buiz
Assistant Examiner—Vy Q. Bui
Attorney, Agent, or Firm—Greenblum & Berstein, P.L.C.

[57] ABSTRACT

An endoscopic grasping tool includes: at least two grasping arms connected with each other at first ends so as to be movable between a closed and an open position of their free ends, the free ends having a form enabling the grasping of a subject, the grasping arms being made of an elastic material. The grasping arms are connected by a link mechanism and the cross section and the length of the grasping arm is designed so that the maximum grasping force at the free ends is in the range of 50–300 g.

7 Claims, 10 Drawing Sheets

ENDOSCOPIC GRASPING TOOL

BACKGROUND OF THE INVENTION

1. Field of the Invention

The invention relates to an endoscopic grasping tool which is used for grasping and recovering a foreign material or the like in a body cavity, with being passed through a treatment tool insertion channel of an endoscope.

The endoscopic grasping tool is roughly classified into two categories, i.e., a tool in which a link mechanism is disposed at a tip end of a sheath to be passed through a treatment tool insertion channel and grasping pieces are opened and closed by the link mechanism, and that in which grasping pieces that are elastically deformable are protruded from and retracted into a tip end of a sheath and, when the grasping pieces are protruded, they are expanded by their own elasticity. The grasping tool of the invention belongs to the former category.

2. Description of the Related Art

In an endoscopic grasping tool wherein grasping pieces are opened and closed by a link mechanism disposed at a tip end of a sheath which is to be passed through a treatment tool insertion channel of an endoscope, usually, the grasping pieces are formed by a pair of beak-like members and a foreign material or the like is grasped and recovered by being nipped between the beak-like grasping pieces.

In the case where a foreign material such as a bean entering a bronchial tube is to be recovered, for example, the foreign material which is nipped between the pair of grasping pieces may be broken by a grasping force. When such a foreign material is once broken, it is very difficult to recover the foreign material.

An endoscopic grasping tool is remotely operated from an operator-side end of a long sheath which is passed through a treatment tool insertion channel. Therefore, a feeling of hardness and the like of a foreign material are hardly transmitted to the hand of the operator.

The operator tends to exert a strong force in order to prevent a foreign material from dropping or to surely grasp the foreign material. In the case where a fragile foreign material or the like such as a bean is to be recovered, therefore, the above-mentioned trouble is liable to occur.

By the way, in an endoscopic grasping tool of a type wherein a grasping piece which is elastically deformable is protruded from or retracted into the tip end of a sheath and which, when protruded, is expanded by its elasticity, the grasping piece is moved in a direction of the retraction into the sheath when a foreign material or the like is grasped. Consequently, a foreign material or the like often fails to be grasped.

Furthermore, in an endoscopic grasping tool of this type, when a foreign material or the like is grasped, the portion of the grasping piece which is outside the sheath becomes very short and hence the grasping piece cannot be elastically deformed to a large degree. This may produce a state where a large grasping force is applied to the foreign material and the foreign material crushes.

SUMMARY OF THE INVENTION

It is an object of the invention to provide an endoscopic grasping tool which can easily surely grasp a fragile foreign material or the like without breaking it.

In order to attain the object, an endoscopic grasping tool includes: at least two grasping arms connected with each other at first ends so as to be movable between a closed and an open position of their free ends, the free ends having a form enabling the grasping of a subject, the grasping arms being made of an elastic material. The grasping arms are connected by a link mechanism and the cross section and the length of the grasping arm is designed so that the maximum grasping force at the free ends is in the range of 50–300 g.

Further, at least one of the grasping arms includes an edge portion surrounding a hole portion defined inside thereof and made of one of metal and plastic. Thus, due to the hole portion, the grasping arm has a high elasticity in an opening and closing direction.

The present disclosure relates to the subject matter contained in Japanese Patent application No. Hei. 9-107063 filed on Apr. 24, 1997 which is expressly incorporated herein by reference in its entirety.

EXPLANATION OF AN ENDOSCOPIC GRASPING TOOL

This explanation will be described with reference to the accompanying drawings.

Figure 2:
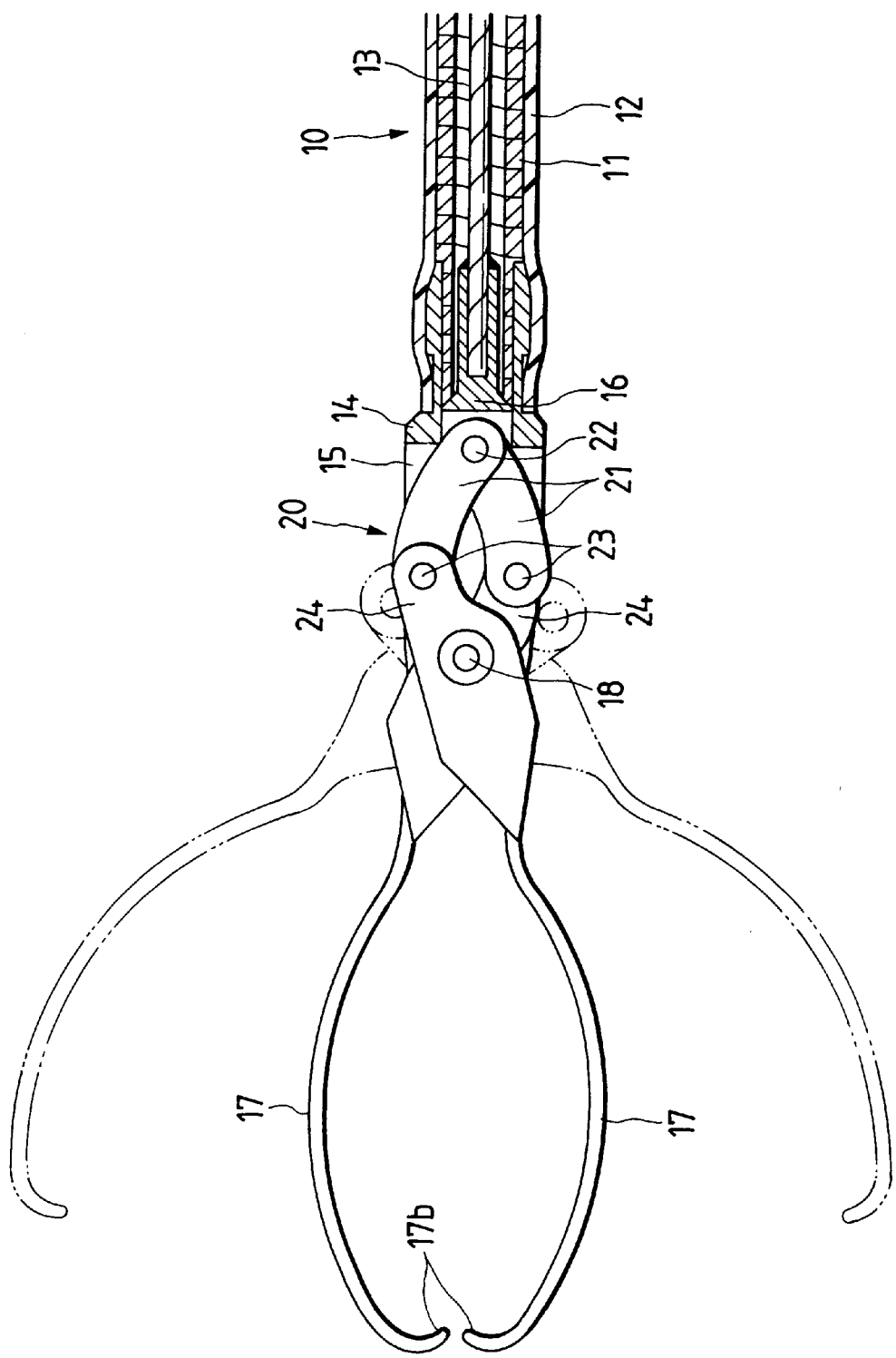
FIG. 2 is a side section view of the tip end portions of the first endoscopic grasping tool.

FIG. 2 shows the tip end portion of a first endoscopic grasping tool. The reference numeral 10 designates a flexible sheath which is to be passed through a treatment tool insertion channel of an endoscope, and which is formed by covering the outer periphery of a close-wound coil pipe 11 made of a stainless steel wire, with an outer tube 12 made of a flexible synthetic resin.

An operating wire 13 is passed through the whole length of the sheath 10 so as to be movable forward and backward in the axial direction. The operating wire 13 is forwardly and backwardly operated by an operation performed on an operation unit (not shown) which is coupled to the operator-side end of the sheath 10.

A tip end body 14 is coupled to the tip end of the sheath 10. A link mechanism 20 is placed in a slit portion 15 which is formed in the tip end body 14. The link mechanism 20 has a pantograph-like shape and is rotatably supported on the tip end body 14 with a support shaft 18.

The tip end of the operating wire 13 is fixedly coupled to a wire coupling member 16 which is coupled to the rear end portion of the link mechanism 20. The link mechanism 20 is operated about the support shaft 18 by moving the operating wire 13 forward and backward in the axial direction.

The reference numeral 21 designates a pair of link pieces constituting the link mechanism 20. The rear ends of the link pieces 21 are coupled to the wire coupling member 16 by a single coupling pin 22, and the tip ends of the link pieces 21 are coupled by coupling pins 23 to link parts 24 which are formed integrally with grasping pieces 17, respectively.

The grasping pieces 17 are formed as a pair of beak-like pieces. The rear ends of the grasping pieces 17 are respectively formed by twisting the link parts 24 so that grasping surfaces of the grasping pieces 17 which the foreign material is abutted are orthogonal to plate-like surfaces 24a of the link parts 24 which confront with each other in parallel. Accordingly, as described above, the pieces 17 are formed integrally with the respective link parts 24. When the link mechanism 20 is operated, therefore, the grasping pieces 17 are opened or closed about the support shaft 18 in accordance with the movement of the link mechanism 20.

In thus configured endoscopic grasping tool, the link mechanism 20 is driven via the operating wire 13 by a remote operation through the operation unit which is coupled to the operator-side end of the sheath 10. The movement of the link mechanism 20 causes the grasping pieces 17 to be opened or closed.

Figure 3:
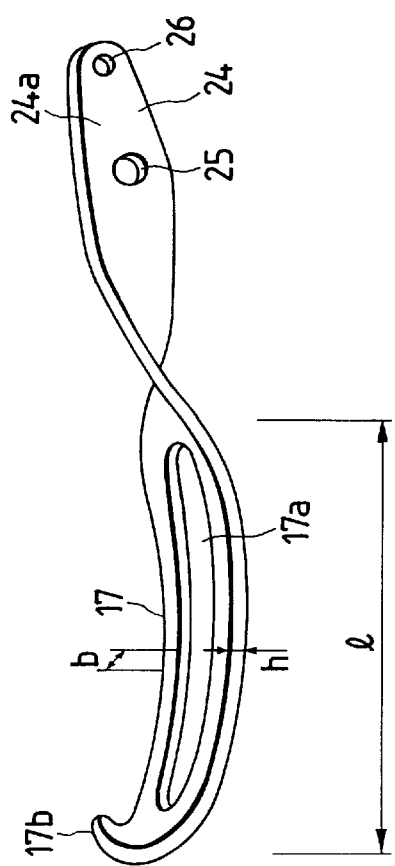
FIG. 3 is a perspective view of a grasping piece of the first grasping tool.

FIG. 3 shows one of the paired grasping pieces 17. The reference numeral 24 designates the link part, 25 designates a shaft hole through which the support shaft 18 is passed, and 26 designates a coupling hole though which one of the coupling pins 23 is passed.

Each of the grasping pieces 17 is made of a thin elastic material such as a metal or plastics, and especially in case of metal, is made of austenitic stainless steel or the like, and in case of plastic, is made of polyethylene, polypropylene, polyacetal, polyimide, nylon or the like. Each of the grasping pieces 17 is formed into a beak-like shape. The tip end portion 17b has a clawlike shape which is inwardly bent.

As shown in FIG. 3, the inner portion 17a of the beak-like external shape is hollowed and only the edge portion is made of a metal material or a plastic material. The edge portion of the grasping pieces 17 surrounding the hollowed inner portion 17a is formed by two thin plate-like members having a rectangular section. The configuration of the grasping pieces 17 is formed so as to have a length l of 8–30 mm, a width b of 0.38–5.37 mm and an thickness h of 0.10–0.38 mm as shown in FIG. 3. The length l is formed to be long, when the section of the edge portion is large, that is, the width b and the thickness h are large, and the length l is formed to be short, when the section of the edge portion is small. Further, in the rectangular section of the edge portion, the width b is formed to be larger than the thickness h. Therefore, the grasping pieces 17 are rich in elasticity, and when an external force in an opening and closing direction of the grasping pieces 17 is applied, the pieces 17 are easily elastically deformed. Accordingly, due to the inner portion 17a, the grasping pieces 17 can have a sufficient grasping force in the opening and closing direction.

In the thus configured endoscopic grasping tool, the grasping pieces 17 are not moved in the axial direction during the opening and closing operations. Even in the case of a remote operation from the end on the operator-side, therefore, a foreign material or the like can be easily grasped between the grasping pieces 17. Furthermore, the grasping pieces 17 can be widely opened. When a polyp or the like is to be removed, therefore, the polyp can be easily grasped.

Figure 1:
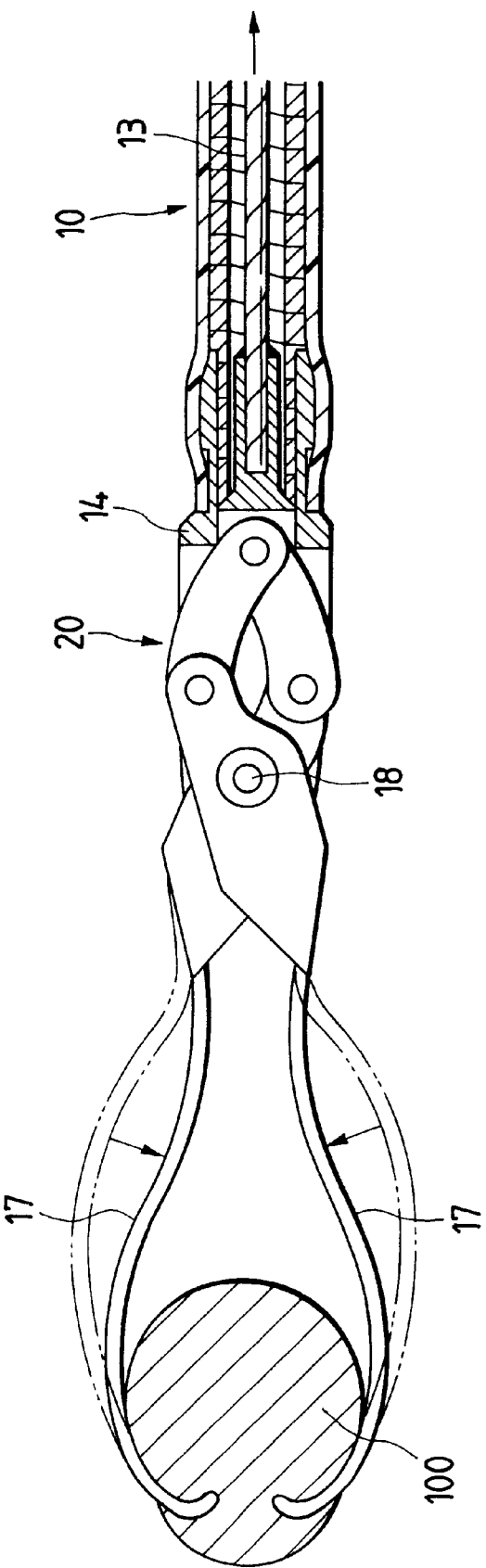
FIG. 1 is a side section view showing a state where a foreign material is grasped between tip end portions of a first endoscopic grasping tool.

As shown in FIG. 1, a foreign material 100 is sandwiched between the pair of grasping pieces 17, and the operating wire 13 is then further pulled by an operation from the operator-side end so as to apply a force for closing the grasping pieces 17. At this time, the grasping pieces 17 are elastically deformed, and hence the foreign material 100 is not broken by the grasping force of the grasping pieces 17.

In general, the grasping pieces 17 is formed so as to have a force which can grasp and does not break the foreign material, that is, to have the maximum grasping force in the range of 50–300 g. In addition, when the grasping tool is used for grasping a soft excision object such as a polyp, the grasping force is set in the range of 50–250 g and when the grasping tool is used for grasping a hard object such as a foreign material in bronchus and a calculus in bile duct, the grasping force is set in the range of 200–300 g.

In order to facilitate such elastic deformation, the grasping pieces 17 are formed into an arcuate shape which is outwardly bulged. As a result, the outer diameter of the grasping pieces 17, that is, the maximum width of the grasping pieces 17 in the opening and closing direction at a closed state, can be formed so as to be larger than the inner diameter of the treatment tool insertion channel of the endoscope.

Figure 4:
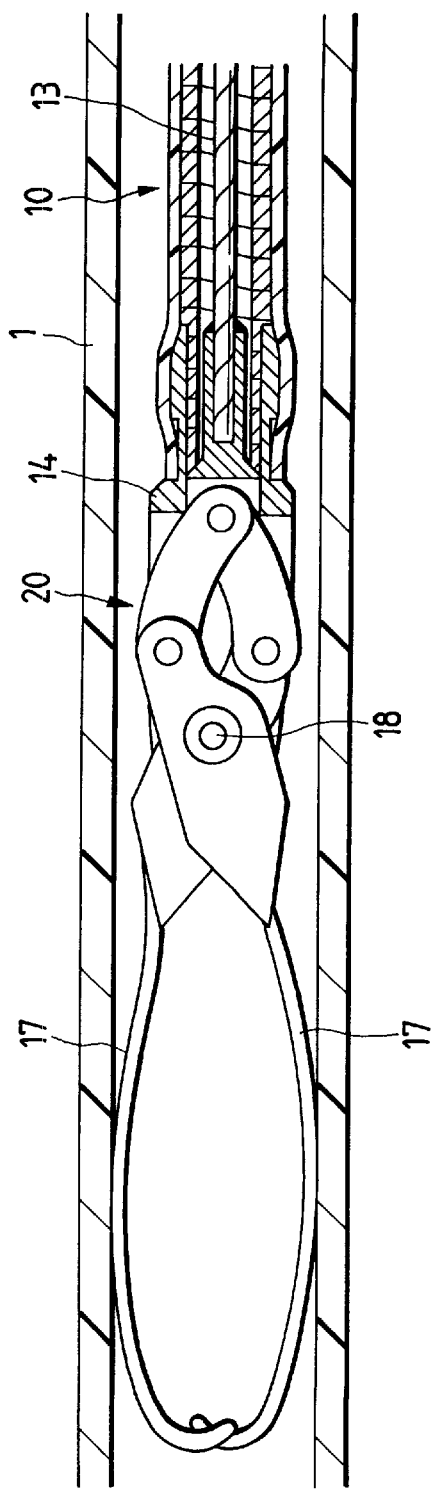
FIG. 4 is a side section view showing a state where the tip end portions of the first endoscopic grasping tool are passed through a treatment tool insertion channel of an endoscope.

In this case, since the grasping pieces 17 are elastically deformable, when the grasping pieces 17 are inserted into the treatment tool insertion channel 1 of the endoscope, therefore, the grasping pieces 17 are caused to have a shape which is lengthened along the inner peripheral face of the treatment tool insertion channel 1 as shown in FIG. 4, so that the width of grasping pieces 17 becomes narrow in the opening and closing direction of the grasping tool. As a result, the grasping pieces 17 can be passed through the treatment tool insertion channel 1. Alternatively, the grasping pieces 17 may have another shape such as that in which plural claws are formed on the tip end portion 17b, or that in which saw-like teeth are formed.

Figure 5A:
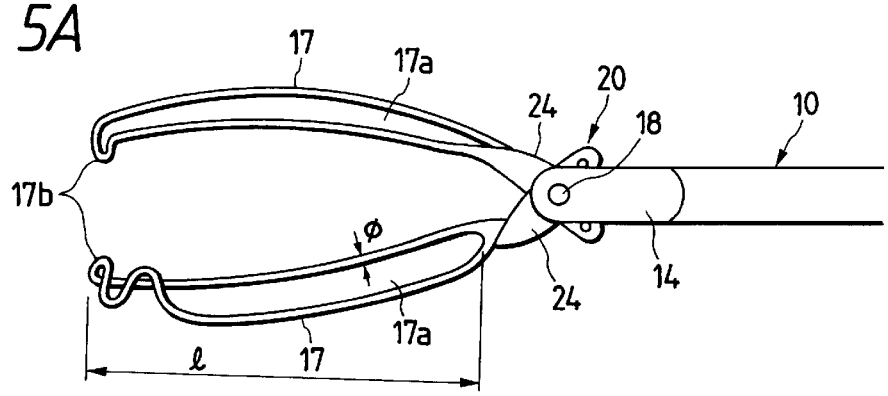
FIG. 5A is a perspective view of a tip end portion of a second endoscopic grasping tool.
Figure 5B:
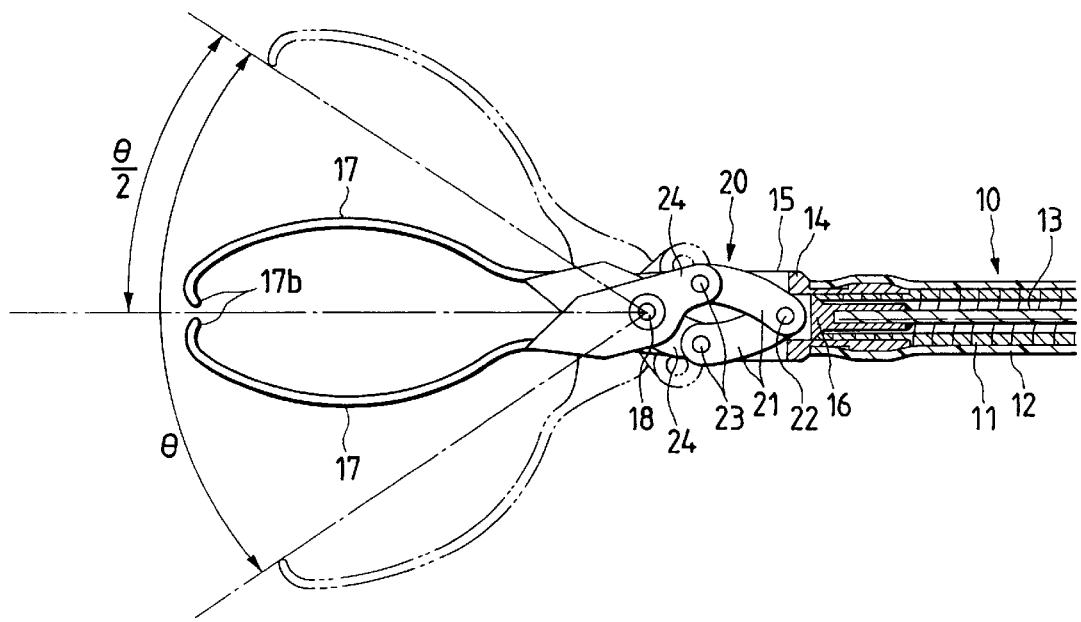
FIG. 5B is a side section view of the tip end portions of the second endoscopic grasping tool.
Figure 5C:
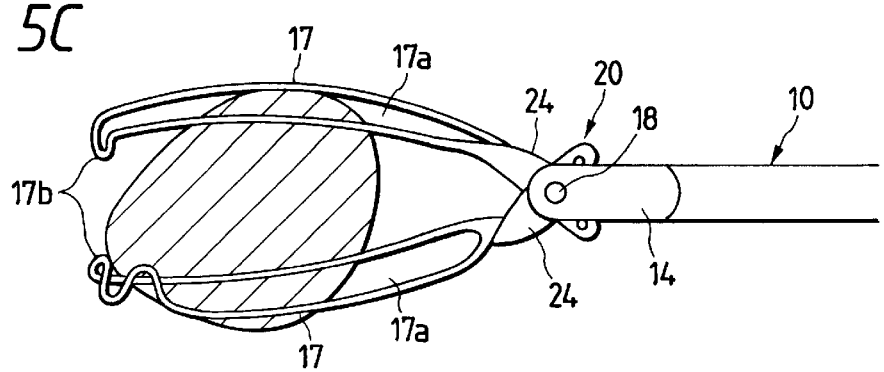
FIG. 5C is a perspective view representing a state which a foreign material is grasped in the second endoscopic grasping tool.

FIGS. 5A to 5C show a second endoscopic grasping tool, and in which the grasping pieces 17 are formed by an elastic metal or plastic material. The grasping pieces 17 are integrally formed by twisting the link parts 24 as well as the first endoscopic grasping tool and further the grasping pieces 17 elongating from the link parts 24 is formed in a wire shape having a circular section. On the other hand, the grasping pieces 17 and the link parts 24 may be connected to each other by welding or the like.

Figure 6:
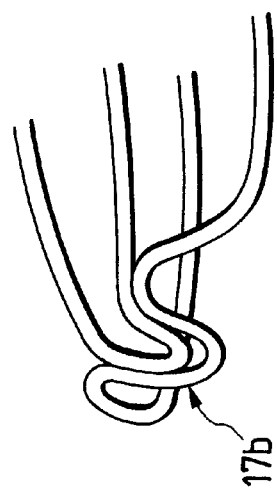
FIG. 6 is an enlarged perspective view of tip end portions of grasping pieces of the second grasping tool.

As shown in FIG. 6 which shows the tip end portions 17b of the grasping pieces 17 in an enlarged manner, the tip end portions are formed so that, in a closed state, a projection of one of the portions is fitted into a recess of the other portion to be engaged therewith. Each of the grasping pieces 17 including the tip end portions 17b can be formed by bending the single wire which has a circular section.

In the second endoscopic grasping tool, in case that the wire having uniform material is applied to the grasping pieces 17, a length l of the grasping pieces 17 is formed short when a diameter φ of the wire is thin, and the length l is formed long when the diameter φ is thick. In addition, when the grasping tool is used for grasping a hard material such as calculus, the diameter of the wire should be thick to some extent and the length should be short, and therefore the opening angle is set to be short. In the thus configured second endoscopic grasping tool, to realize the maximum grasping force in the range of 50–300 g, the configuration of the grasping pieces 17 is formed so as to have the length l of 8–30 mm, the diameter φ of 0.2–0.45 mm and an maximum opening angle θ of 30–60° by a wire of austenite stainless steel as shown in FIGS. 5A and 5B.

Here, the following table 1 represents a relation of a configuration of the wire and a maximum grasping force which is applied at the tip end portion thereof when grasping a foreign material strongly as shown in FIG. 5C. The maximum grasping force represents a force necessary for recovering the grasping pieces to a closed state shown in FIG. 5B when one of the grasping pieces is spread from the closed state to an opening angle θ/2 being a maximum opened state by the external force. In addition, since the recovering force is measured at the tip end portions of the grasping pieces 17, according to the principles of the lever, the grasping force at the tip end portions is minimum and the grasping force is increased as approaching the measured point to the support shaft 18 of the grasping pieces 17.

TABLE 1

| | Diameter φ (mm) | Length l (mm) | Maximum opening angle of one grasping piece θ/2 (°) | Maximum grasping force (g) |
| --- | --- | --- | --- | --- |
| Grasping tool for grasping a polyp or the like | 0.3 | 15 | 30 | 80 |
| | 0.3 | 20 | 30 | 50 |
| | 0.4 | 30 | 30 | 70 |
| Grasping tool for grasping a calculus or the like | 0.4 | 15 | 15 | 250 |

Figure 7:
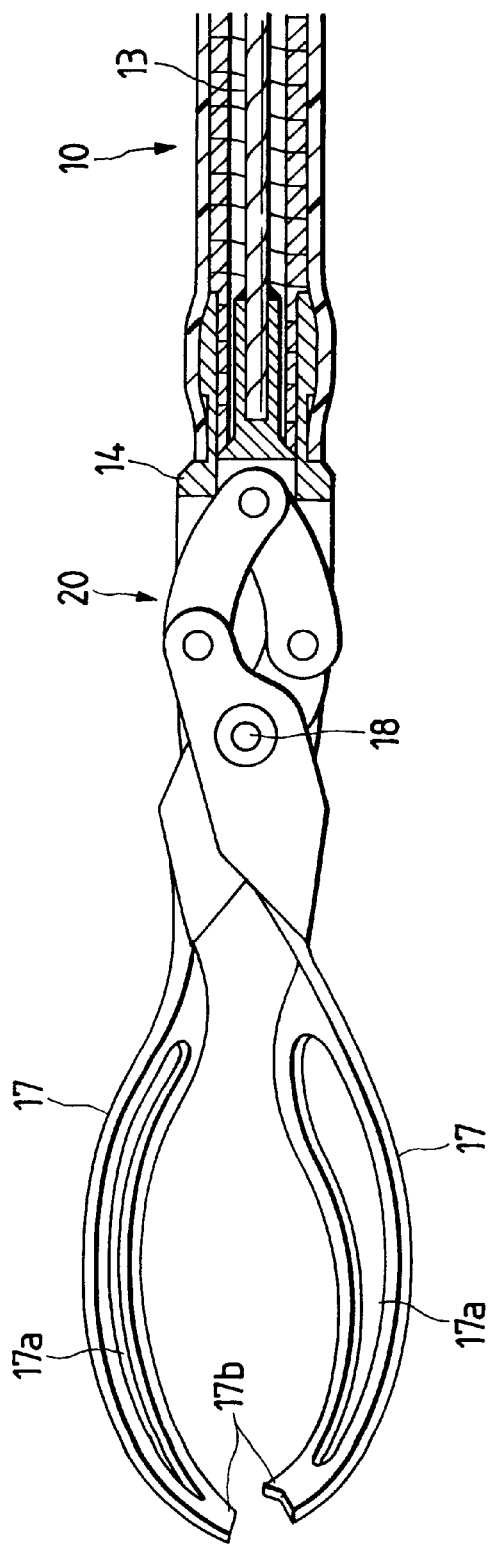
FIG. 7 is a side section view of the tip end portions of a third endoscopic grasping tool.
Figure 8:
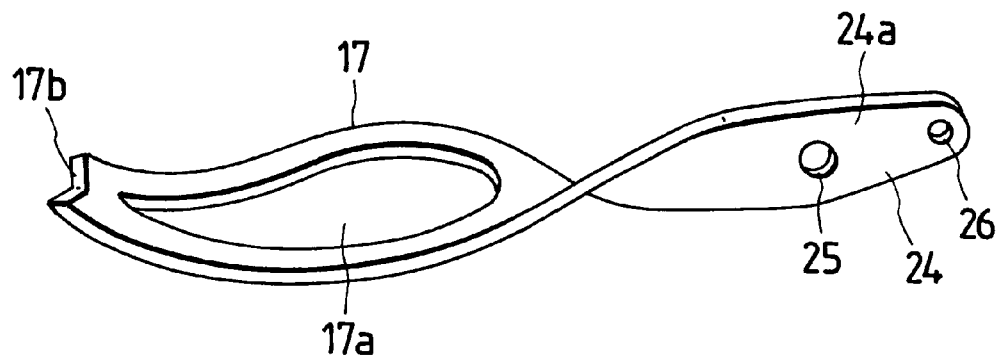
FIG. 8 is a perspective view of a grasping piece of the third grasping tool.

FIG. 7 shows a third endoscopic grasping tool, and in which, as shown in FIG. 8, the grasping pieces 17 are formed so as to be bulged also in a lateral direction which is orthogonal to the opening and closing direction of the grasping pieces 17 and the axial direction. According to this configuration, the grasping pieces 17 exhibit a further high elasticity in the lateral direction as compared with an another endoscopic grasping tool. Therefore, the possibility that, when the foreign material 100 is grasped, the foreign material 100 is crushed is further lowered.

In the third embodiment, the rear ends of the grasping pieces 17 are respectively formed by twisting the link parts 24 so that grasping surfaces of the grasping pieces 17 which the foreign material is abutted are orthogonal to plate-like surfaces 24a of the link parts 24 which confront with each other in parallel. Accordingly, the pieces 17 are formed integrally with the respective link parts 24.

The tip end portions 17b of the grasping pieces 17 are also formed so that, in a closed state, a projection of one of the portions is fitted into a recess of the other portion to be engaged therewith.

Figure 9:
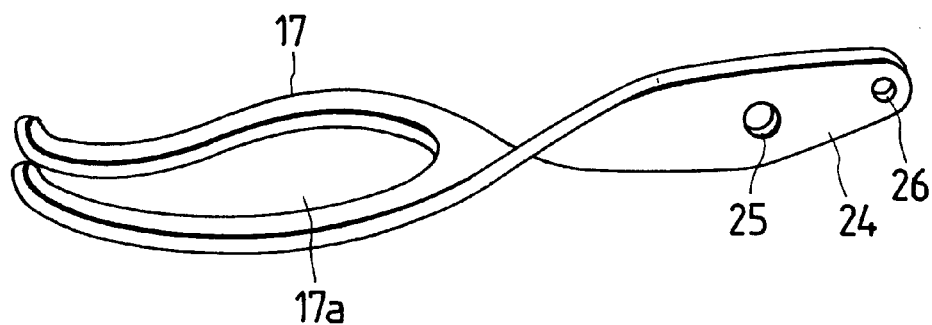
FIG. 9 is a perspective view of a grasping piece of a fourth grasping tool.
Figure 10:
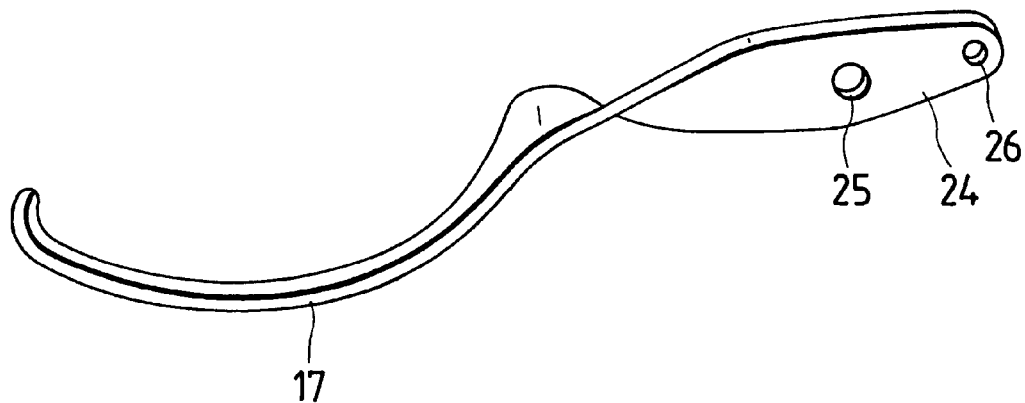
FIG. 10 is a perspective view of a grasping piece of a fifth grasping tool.

Each of the grasping pieces 17 of the embodiment shown in FIG. 7 may be formed as two thin plate-like members which are separated from each other at their tip end portions as shown in a fourth grasping tool of FIG. 9. In addition, as shown in a fifth grasping tool of FIG. 10, the grasping piece may be formed as a single thin plate-like member.

Figure 11:
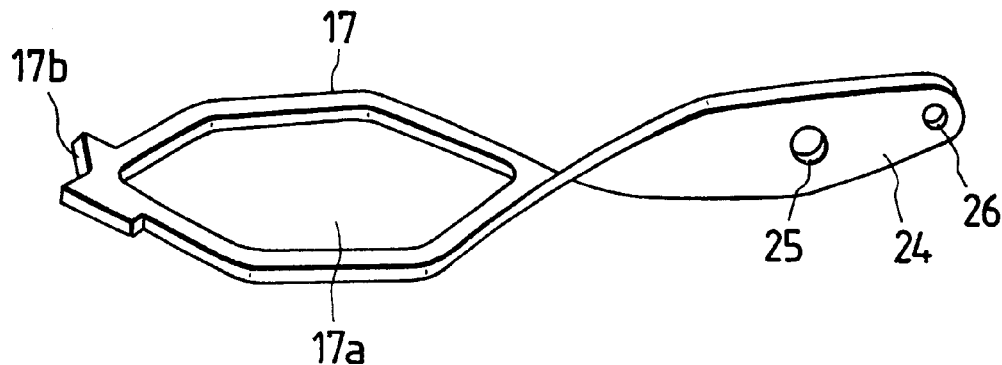
FIG. 11 is a perspective view of a grasping piece of a sixth grasping tool.

As shown in a sixth grasping tool of FIG. 11, each of the grasping pieces 17 may be formed into a polygonal shape. In addition, the tip end portions 17b of the grasping pieces 17 are also formed so that, in a closed state, a projection of one of the portions is fitted into a recess of the other portion to be engaged therewith.

In the fourth to sixth endoscopic grasping tools, the grasping pieces 17 are also formed by twisting the link parts 24 as well as the first and second grasping tools. Further, in the third to sixth grasping tools, since the edge portion is formed so as to have a configuration (width b, thickness h, length l) of the first grasping tool, the grasping pieces 17 can have a sufficient elasticity in the opening and closing direction.

Figure 12:
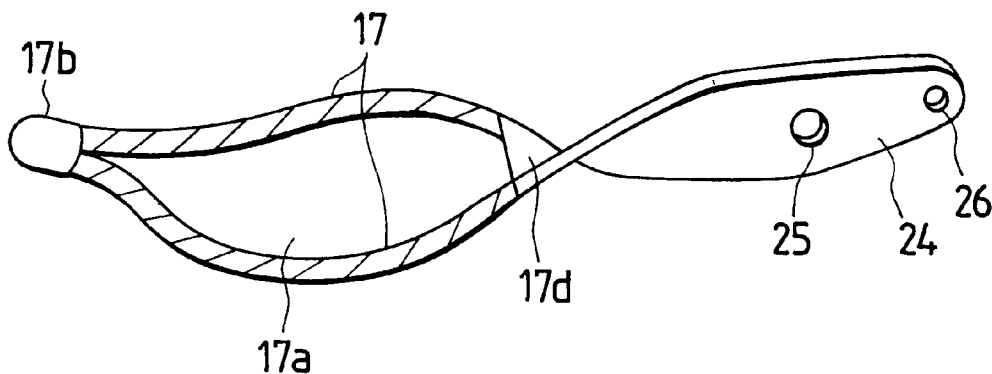
FIG. 12 is a perspective view of a grasping piece of a seventh grasping tool.

In addition, as shown in a seventh grasping tool of FIG. 12, the grasping pieces 17 is a stranded wire formed by stranding a plurality of wires made of stainless steel or the like.

In the seventh grasping tool, the tip end portions of the two grasping pieces 17 are gathered into one piece by a cylindrical tip end chip 17c. The joint between the grasping pieces 17 formed by stranded wires and the link part 24 formed by a plate member may be realized by twisting the tip ends of the link parts 24, so as to form rear end portions 17d of the grasping pieces 17 and then brazing, laser welding, or the like between the stranded wires and the rear ends 17d.

Figure 13:
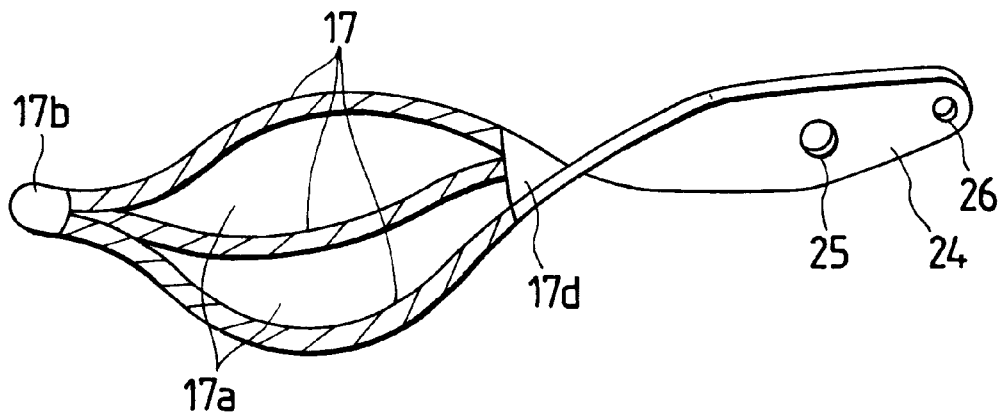
FIG. 13 is a perspective view of a grasping piece of an eighth grasping tool.
Figure 14:
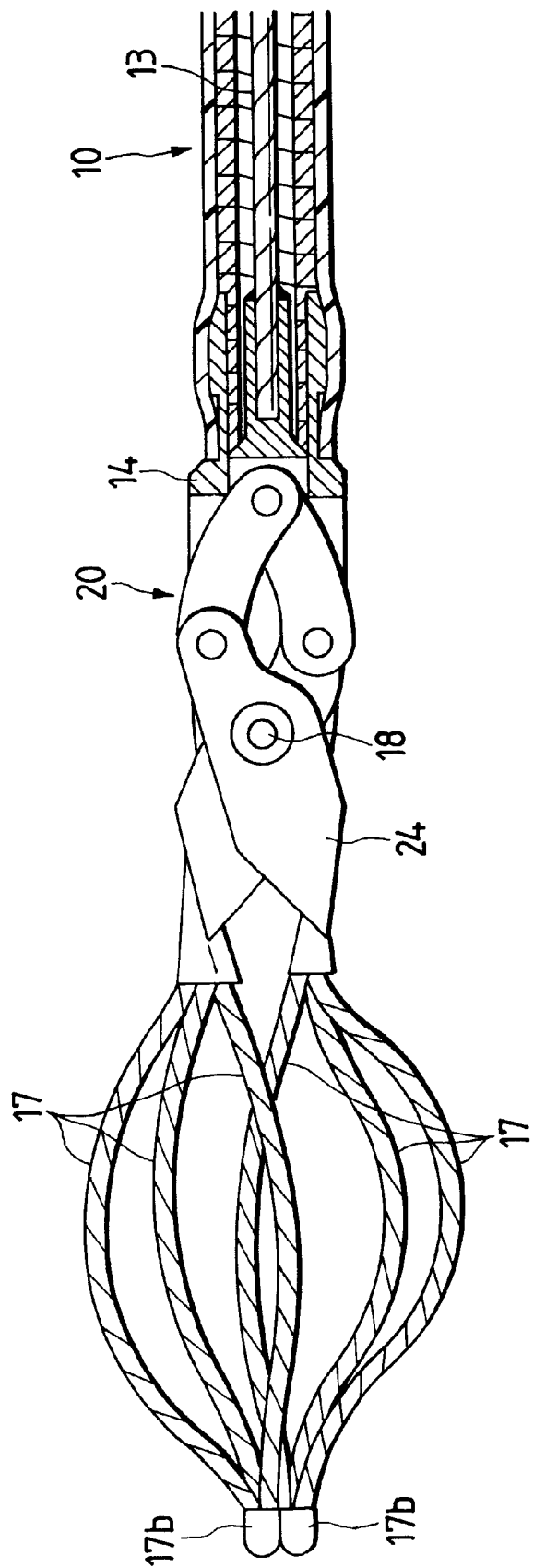
FIG. 14 is a side section view of a tip end portion of the eighth endoscopic grasping tool.

As shown in an eighth grasping tool of FIG. 13, each grasping piece 17 may be configured so that a third stranded wire is further disposed in the middle part of the hollowed inner portion 17a. The joint between the grasping pieces 17 formed by stranded wires and the link part 24 formed by a plate member can be realized as well as the seventh grasping tool. FIG. 14 shows the tip end portion of an endoscopic grasping tool into which such grasping pieces 17 each consisting of three stranded wires are incorporated.

Figure 15:
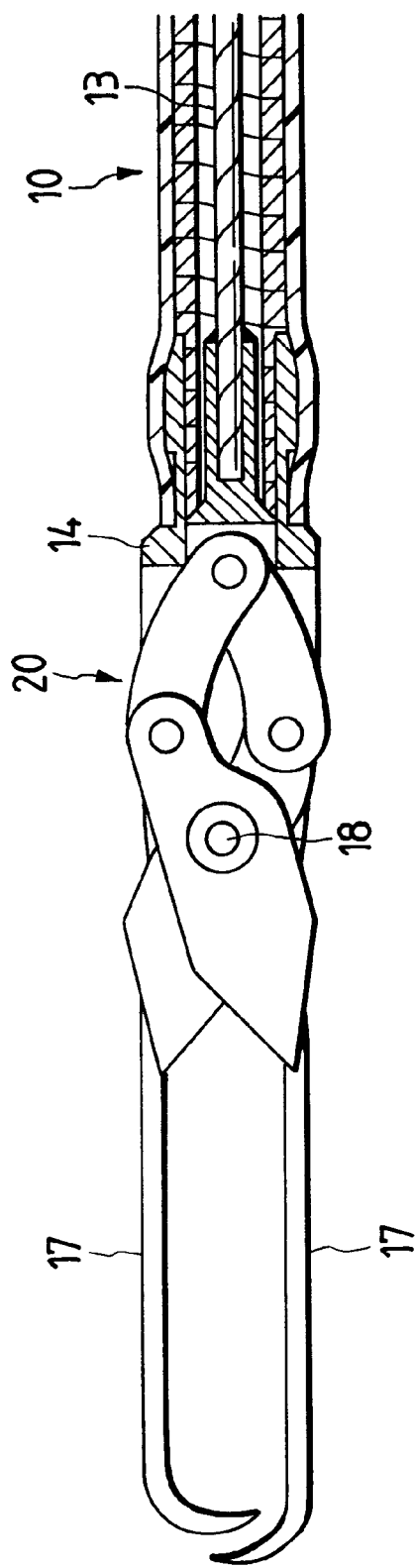
FIG. 15 is a side section view of a tip end portion of a ninth endoscopic grasping tool.
Figure 16:
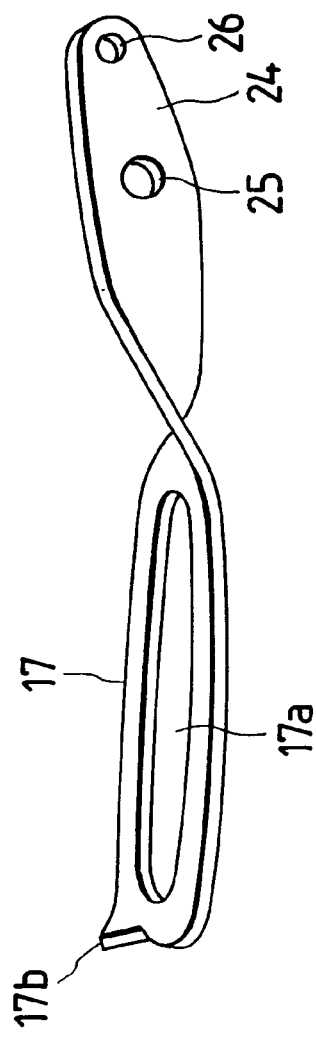
FIG. 16 is a perspective view of a grasping piece of the ninth grasping tool.

FIG. 15 shows the tip end portion of a ninth endoscopic grasping tool. In the ninth grasping tool, the grasping pieces 17 are not outwardly bulged in the opening and closing direction of the grasping pieces 17 but formed into a flat shape. In addition, the grasping pieces 17 are formed by twisting the link parts 24 as well as the first grasping tool. As shown in FIG. 16, the hollowed inner portion 17a is defined by the edge portion having the same configuration as that of the first grasping tool and, the hollowed inner portion 17a is formed also in each of the grasping pieces 17, so that the grasping pieces 17 have sufficient elasticity in the opening and closing direction and the lateral direction. The tip end portions 17b of the grasping pieces 17 are also formed so that, in a closed state, a projection of one of the portions is fitted into a recess of the other portion to be engaged therewith.

Figure 17:
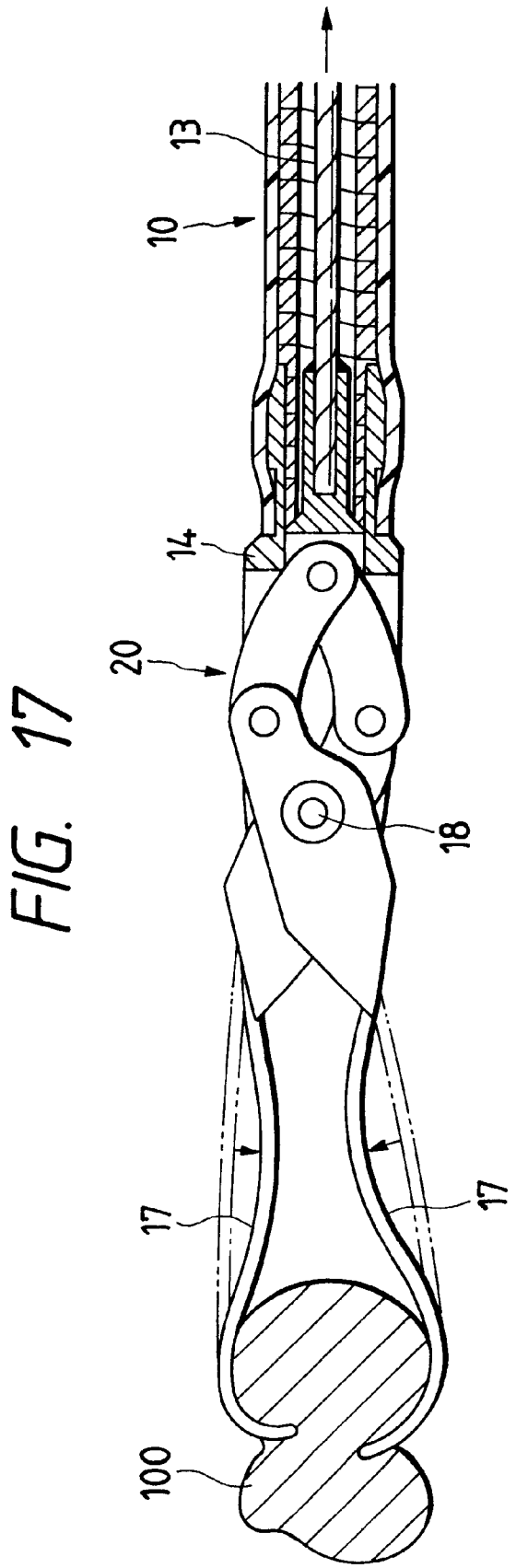
FIG. 17 is a side section view showing a state where a foreign material is grasped between tip end portions of the ninth endoscopic grasping tool.

Even when, as shown in FIG. 17, a foreign material 100 is sandwiched between the pair of grasping pieces 17 and the operating wire 13 is then further pulled by an operation from the operator-side end so as to apply a force for closing the grasping pieces 17, therefore, the grasping pieces 17 themselves are elastically deformed, and hence the foreign material 100 is not broken.

In the third to ninth endoscopic grasping tools, the configuration of the grasping piece is formed in such a manner that the length of the edge portion is long when the section thereof is large, and the length of the edge portion is short when the section thereof is small, as well as the first and second endoscopic grasping tools.

According to the invention, the grasping pieces are made of a material of high elasticity. Even when a foreign material or the like is sandwiched between the grasping pieces and further a closing force is then applied to the grasping pieces, therefore, the grasping pieces themselves are elastically deformed, so that a fragile foreign material or the like can be easily surely grasped without breaking the foreign material.

Further, according to the invention, since the inner portion is hollowed inside each of the grasping pieces, the grasping pieces are elastically deformed in the opening and closing direction easily.

What is claimed is:

1. An endoscopic grasping tool comprising:

at least two grasping arms connected with each other at first ends so as to be movable between a closed and an open position at their free ends, said free ends having a form enabling the grasping of an object, the grasping arms being made of an elastic material and being connected by a link mechanism, each of said grasping arms including a link part of said link mechanism, each of said link parts including a rotational axis, said grasping arms being pivotal about said rotational axis between said closed and open positions, at least one of said grasping arms includes a hole portion formed substantially throughout the entire length between said first end and said free end and an edge portion surrounding said hole portion, said at least one of the grasping arms being formed in an arcuate shape so as to bulge outwardly in a lateral direction throughout substantially the entire length between said first end and said free end of the grasping arm, and the cross section and the length of the grasping arm being designed so that the maximum grasping force at said free ends is in the range of 50–300 g, whereby said at least one of the grasping arms has a high elasticity in an opening and closing direction.

2. The endoscopic grasping tool according to claim 1, wherein the elastic material constituting the grasping arm forms a part of said link mechanism by twisting the elastic material, whereby the grasping arm is integrally formed with said link mechanism.

3. The endoscopic grasping tool according to claim 1, wherein at least one of the grasping arms is made of one of metal and plastic.

4. The endoscopic grasping tool according to claim 1, wherein the cross section of said edge portion of the grasping arm has a rectangular shape being a width of 0.38–5.37 mm and a thickness of 0.10–0.38 mm, and the grasping arm has a length of 8–30 mm.

5. The endoscopic grasping tool according to claim 1, wherein said edge portion of the grasping arm is formed by a wire member having a diameter of 0.2–0.45 mm, and a length of the wire member is set so that the grasping arm has a length of 8–30 mm.

6. A endoscopic grasping tool according to claim 1, wherein at least one of the grasping arms is formed by a stranded wire.

7. A endoscopic grasping tool according to claim 1, wherein one of the grasping arm has a projection at a tip end portion and the other of the grasping arm has a recess at a tip end portion so that the tip end portions of the grasping arms engage with each other in a state where the grasping arms are closed.

* * * * *